US010363375B2

(12) United States Patent
Orofino (10) Patent No.: US 10,363,375 B2
(45) Date of Patent: Jul. 30, 2019

(54) PRE-FILLED INJECTION DEVICE (71) Applicant: OROFINO PHARMACEUTICALS GROUP S.r.l., Rome (IT)

(72) Inventor: Ernesto Orofino, Rome (IT)

(73) Assignee: OROFINO PHARMACEUTICALS GROUP S.r.l., Rome (IT)

( * ) Notice: Subject to any disclaimer, the term of this patent is extended or adjusted under 35 U.S.C. 154(b) by 94 days.

(21) Appl. No.: 15/326,969

(22) PCT Filed: Jun. 17, 2015

(86) PCT No.: PCT/IB2015/054569
§ 371 (c)(1),
(2) Date: Jan. 17, 2017

(87) PCT Pub. No.: WO2016/012878
PCT Pub. Date: Jan. 28, 2016

(65) Prior Publication Data
US 2017/0203047 A1     Jul. 20, 2017

(30) Foreign Application Priority Data
Jul. 22, 2014 (IT) .............................. RM2014A0408

(51) Int. Cl.
*A61M 5/19* (2006.01)
*A61M 5/315* (2006.01)
(Continued)

(52) U.S. Cl.
CPC ........ *A61M 5/31596* (2013.01); *A61M 5/204* (2013.01); *A61M 5/284* (2013.01); *A61M 5/31565* (2013.01); *A61M 5/31578* (2013.01)

(58) Field of Classification Search
CPC ............. A61M 5/204; A61M 5/31565; A61M 5/31578; A61M 2005/131598;
(Continued)

(56) References Cited

U.S. PATENT DOCUMENTS 5,637,100 A * 6/1997 Sudo ...................... A61M 5/284
                                                      604/218
7,727,183 B2 * 6/2010 Sharon .................... A61M 5/24
                                                      604/89
(Continued)

FOREIGN PATENT DOCUMENTS

EP          0 815 886 A2     1/1998
WO       2006/003653 A2      1/2006
WO    WO-2006003653 A2 *     1/2006    .............. A61M 5/24

OTHER PUBLICATIONS

International Search Report and Written Opinion of the International Searching Authority for corresponding International Patent Application No. PCT/IB2015/054569 dated Aug. 28, 2015, 8 pgs.

*Primary Examiner* — Amber R Stiles
*Assistant Examiner* — Nicholas J Chidiac
(74) *Attorney, Agent, or Firm* — Merchant & Gould P.C.

(57) ABSTRACT

A pre-filled injection device includes a tubular containment body extending between a first and second openings, inside which are hermetically separated first and second containment chambers. A first substance is contained in the first containment chamber. First and second plugs inside the tubular body define the second containment chamber, and slide inside the tubular body. A second liquid substance inside the second containment chamber is intended to be mixed inside the tubular body with the first substance for reconstituting an injectable solution. A dosing reservoir has an inlet and an outlet, the inlet being in communication with the first containment chamber so that the first containment chamber extends between the first plug and the dosing reservoir inlet. The dosing reservoir contains a fraction of the injectable solution. The first plug includes a projecting appendix passing through and entering the dosing reservoir to eject the fraction of solution.

15 Claims, 7 Drawing Sheets

(51) Int. Cl.
*A61M 5/20* (2006.01)
*A61M 5/28* (2006.01)

(58) Field of Classification Search
CPC .... A61M 5/131596; A61M 2005/1787; A61M 2005/3128; A61M 2005/3123; A61M 5/284; A61M 2005/31598; A61M 5/31596; A61M 5/31533; A61J 1/2093
USPC .......................................................... 604/186
See application file for complete search history.

(56) References Cited

U.S. PATENT DOCUMENTS

| | | | |
|---|---|---|---|
| 2004/0133163 A1* | 7/2004 | Schiffmann | A61M 5/30 604/131 |
| 2004/0267201 A1* | 12/2004 | Agerup | A61M 5/14216 604/152 |
| 2008/0082044 A1* | 4/2008 | Sharon | A61M 5/24 604/89 |
| 2012/0136298 A1* | 5/2012 | Bendix | A61M 5/2448 604/89 |
| 2014/0128817 A1 | 5/2014 | Davies et al. | |

* cited by examiner

400408, filed 22 Jul. 2014, and which applications are incorporated herein by reference. To the extent appropriate, a claim of priority is made to each of the above disclosed applications.

BACKGROUND OF THE INVENTION

The present description refers to the technical field of syringes or injection cartridges and particularly concerns a pre-filled injection device.

The pre-filled syringes or cartridges, for example the double chamber ones, are known for a long time and nowadays they are used widely. Said double chamber syringes or cartridges include a tubular containment body and two substances, at least one of which is a liquid substance, contained in two initially separated containment chambers, which are defined inside the tubular body.

The two substances, which are for example a solid substance in a powder form and a liquid substance, are intended to be mixed just before being administered/injected to the patient. The liquid substance is for example an injectable solvent. In order to mix the two substances, the two containment chambers are brought in communication in order to reconstruct an injectable solution, for example by providing for a bypass element between the two chambers in the pre-filled syringe or cartridge.

Currently, no pre-filled syringes are known allowing administering/injecting very small doses of a reconstituted solution, for example doses having a volume of about one milliliter or a tenth milliliter. Those doses are required for example to administer antibiotics locally, for example to inject a cephalosporin antibiotic, such as cefuroxime, in the patient's ocular chamber.

There is the need of making a pre-filled injection device, which allows injecting very small doses of a reconstituted solution in an accurate and safe way.

SUMMARY OF THE INVENTION

A general object of the present description is to make a pre-filled injection device available, which allows fulfilling said need.

BRIEF DESCRIPTION OF THE DRAWINGS

The invention will be better understood from the following detailed description of its embodiments, made by way of non-limitative example relating to the attached drawings, where.

DETAILED DESCRIPTION OF THE DRAWINGS

In the attached figures, same or similar elements will be specified by the same reference numerals.

Referring to FIGS. 1 to 6, there is depicted a first embodiment of a pre-filled injection device 1, which is, in the particular example being depicted, a pre-filled double chamber syringe. In one alternative embodiment, the pre-filled injection device 1 is a pre-filled cartridge. In further embodiments there can be provided for more than two chambers in the pre-filled injection device 1. The pre-filled injection device 1 allows the reconstitution of an injectable solution and injecting a very small dose of said solution, for example, injecting a solution quantity less than 1 milliliter and preferably equal, or almost equal, to 0.1 milliliters. Preferably, said dose is less than about ¹⁄₂₅ of the injectable solution being reconstituted inside the pre-filled injection device 1 and preferably equal to ¹⁄₅₀ of the reconstituted injectable solution.

Figure 1:
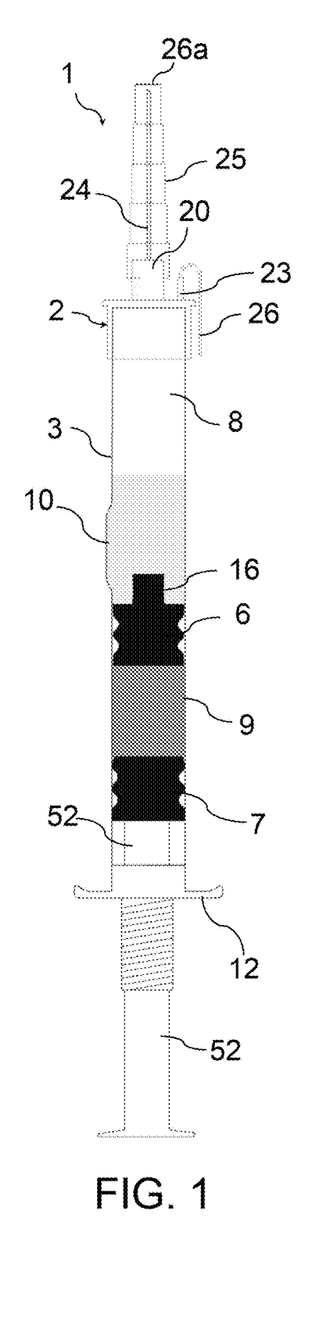
FIG. 1 shows a lateral view of a first embodiment of a pre-filled injection device wherein said device is shown in a first operating configuration.
Figures 2, 3:
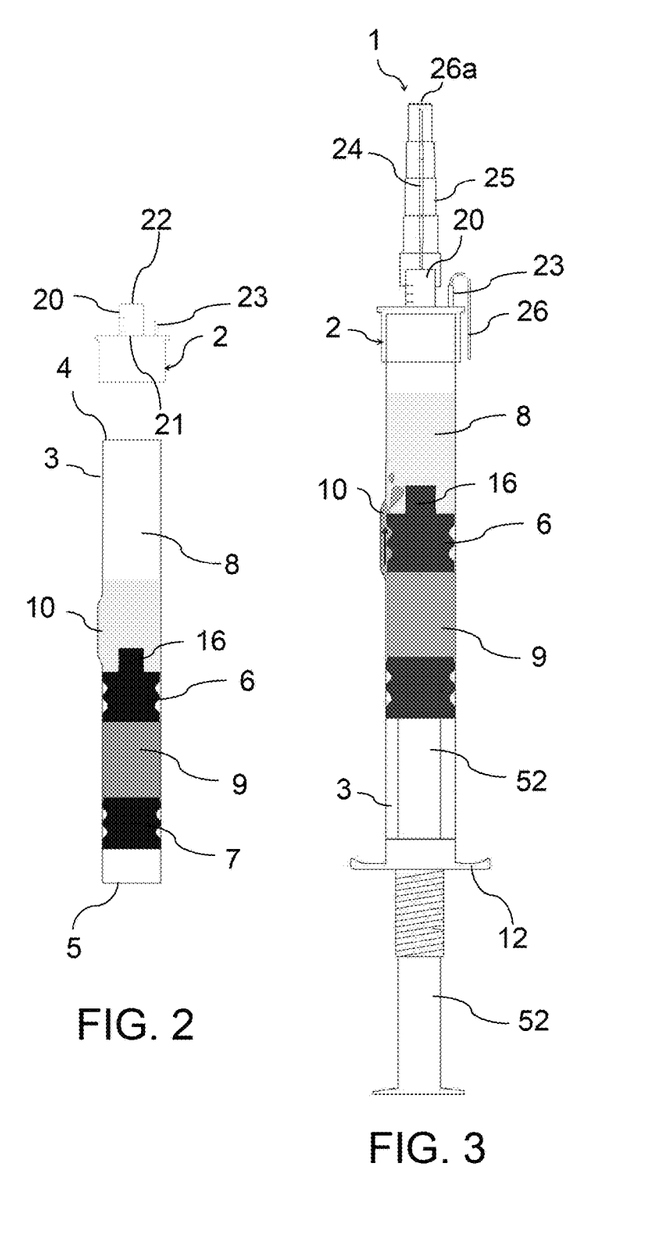
FIG. 2 shows a lateral view of some detached parts of the injection device of FIG. 1.
FIG. 3 shows a lateral view of the injection device of FIG. 1 wherein said device is shown in a second operating configuration.

Referring to FIG. 2, the pre-filled injection device 1 includes a tubular containment body 3, extending between a first opening 4, or front opening, and a second opening 5, or back opening 5. Inside the tubular body 3, in the operating configuration depicted in FIG. 1, named "initial configuration", there are defined a first 8 and a second 9 containment chamber which are hermetically separated from one another. The first containment chamber 8 will be named front chamber while the second containment chamber 9 will be named back chamber.

Preferably, the pre-filled injection device 1 includes a closure device 2 fastened to the tubular body 3, for example fastened to the external lateral walls of the tubular body 3 at one end portion of the first containment chamber 8. According to one alternative embodiment, the closure device 2 is integral to the tubular body 3 and thus it is an end portion of the tubular body 3. Preferably, the pre-filled injection device 1 includes an ergonomic grip section 12 on the opposite side with respect to the closure device 2, which section is fastened to the tubular body 3 or is integral to the tubular body 3.

The tubular body 3 is for example in the form of a containment body of a syringe or a cartridge being suitable to contain injectable substances and it is preferably made of glass or plastic material that is transparent or substantially transparent. Preferably, the tubular body 3 is made as a single piece.

The pre-filled injection device 1 includes:

a first solid or liquid substance, contained in the first containment chamber 8;

a first 6 and a second 7 plugs, arranged inside the tubular body 3, so as to define therebetween in the tubular body 3 the second containment chamber 9, and adapted to slide inside the tubular body 3 (for example, due to a pushing or pulling force);

a liquid second substance, contained inside the second containment chamber 9, intended to be mixed inside the tubular body 3 with the first substance for the reconstitution of an injectable solution.

Preferably, the first substance is a highly active substance.

The first substance is for example a powder, a granulated substance, a sterile tablet or a pressed powder. Said first substance can be or can contain an API. According to one embodiment, the first substance includes two different substances for example in the form of two different tablets, each including one of said two different substances.

In a case where the first substance is solid, this can be a crystallized or lyophilized substance. The version where the first substance is crystallized and not lyophilized is currently the preferred one. In a case where the first substance is a lyophilized powder, it is preferred that said powder is obtained by means of a lyophilization process being carried out before inserting the first substance into the first containment chamber 8.

Said first substance is for example a highly active substance, such as a beta-lactam antibiotic, or a cephalosporin antibiotic or a cytotoxic antitumor or a hormone or a biological preparation. Said first substance can be also a normal active ingredient, namely an ingredient that cannot be defined as being highly active.

Plugs 6, 7 are made of plastic material, for example, they hermetically engage to the internal walls of the tubular body 3 and they can slide inside the tubular body 3 under the action of an external pushing or pulling force.

Preferably, said second liquid substance is an injectable solvent, for example a solvent WFI (Water For Injection) or a lidocaine solution or a water and benzyl alcohol solution or a sodium chloride physiological solution or in general any injectable substance adapted to reconstruct another solid or liquid substance. The second liquid substance can be or can include an API (Active Pharmaceutical Ingredient).

According to one embodiment, the first plug 6, also named intermediate plug 6, includes at least one bypass channel being initially in a closed state and being adapted to be led to an open state following the application of an external force, for example a pushing force on the plug. Plugs having bypass channels are generally known to those skilled in the art in the sector of pre-filled injection devices and therefore they will not be further described.

According to one alternative embodiment, the containment body 3 includes an internal wall provided with a recess 10 being adapted to define a bypass channel. In the initial configuration depicted in FIG. 1, that recess is arranged between the first plug 6 and the first opening 4.

Preferably, the second plug 7, or back plug 7, includes a fastening element adapted to fasten a plunger 52 to the second plug 7 so that the second plug 7 can slide inside the tubular body 3 under the pushing or pulling action of plunger 52. Said fastening element includes for example an internally threaded blind hole made in the thickness of the second plug 7, inside which a complementary threaded end portion of plunger 52 can be inserted and screwed.

The first plug 6 is separated from the first opening 4 in order to delimit the first containment chamber 8, or front chamber 8, between the first plug 6 and the first opening 4.

The pre-filled injection device 1 also includes a dosing reservoir 20, having an inlet opening 21 and an outlet opening 22. The inlet opening 21 is in communication with the first containment chamber 8 so that the first containment chamber 8 extends between the first plug 6 and the inlet opening 21 of the dosing reservoir 20. In the depicted particular example, the dosing reservoir 20 is defined inside the closure device 2, but in one different embodiment, it could be part of the same tubular body 3 and be basically a narrowing of the first containment chamber 8.

According to one embodiment, the dosing reservoir is made of a transparent or translucent material so that it is possible to see its content from outside and preferably, it includes a graduated scale that is also visible from outside.

According to one preferred embodiment, the pre-filled injection device 1 includes one needle 24 whose internal channel is in fluid communication with the outlet opening 22 of the dosing reservoir 20. For example, the needle 24 is fastened to the dosing reservoir 20 on the opposite side with respect to the first containment chamber 8. Preferably, the pre-filled injection device 1 includes a protective shield 25 for the needle 24. Preferably, the protective shield 25 is a telescopic shield formed by a plurality of axially aligned sections which, starting form an initial configuration being shown, for example, in FIG. 1, can be led to an open configuration being shown, for example, in FIG. 5. According to one possible embodiment, the protective shield 25 has an end portion being sealed by a removable and/or pierceable membrane or sheet 26a.

Starting from the initial configuration of FIG. 1, as a result of a pushing action of plunger 52, for example due to a manual operation of plunger 52, the first 6 and second 7 plugs are adapted to slide in the tubular body 3 until reaching a so-called reconstitution configuration, being depicted in FIG. 3, where, thanks to bypass 10, the two containment chambers 8 and 9 are communicating each other and the second substance 9 enters the first chamber 8 in order to mix together with the first substance. In said reconstitution configuration, shaking the pre-filled injection device 1, for example manually, can ease the mixing of the two substances.

Figure 4:
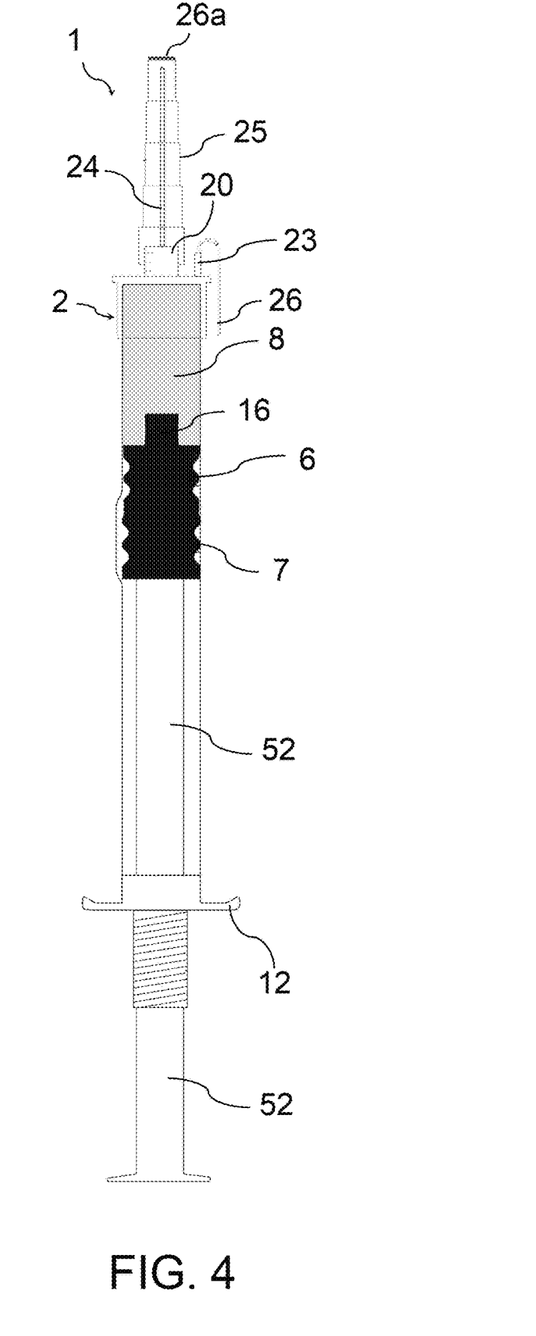
FIG. 4 shows a lateral view of the injection device of FIG. 1 wherein said device is shown in a third operating configuration.

Starting from the operating configuration of FIG. 3, while holding the pre-filled injection device 1 with the reservoir 20 oriented upwards and further pushing the plunger 52, it is possible to further move both plugs 6 and 7 forward until said plugs come into contact with each other, to eject the air existing in the first containment chamber 8 until reaching the operating configuration of FIG. 4, named "end of air ejection" configuration.

Figure 5:
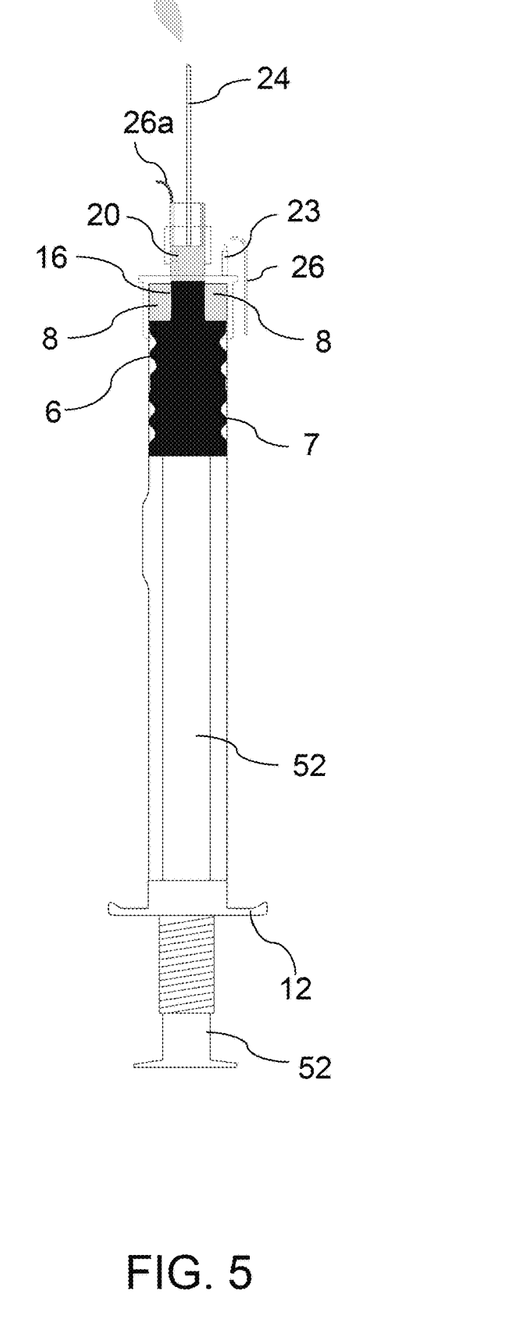
FIG. 5 shows a lateral view of the injection device of FIG. 1 wherein said device is shown in a fourth operating configuration.

Starting from the end of air ejection configuration of FIG. 4, still under the pushing action of plunger 52, after suitably moving the protective shield 25 in the open configuration, it is possible to slide the first plug 6 (under the pushing action of second plug 7 being pushed in turn by plunger 52) in order to reduce the volume of the first containment chamber 8 and eject a fraction of the reconstituted solution (from now on being named "first fraction") from tubular body 3 through the outlet opening 22 of the dosing reservoir 20 until reaching a so-called pre-administering configuration being depicted in FIG. 5, wherein:

the first plug 6 closes the inlet opening of the dosing reservoir 20;

a fraction of the reconstituted solution (from now on being named "second fraction") is contained in the first containment chamber 8; and the dosing reservoir 20 is filled with a fraction of the reconstituted solution (from now on being named "third fraction") being the solution dose to be administered to the patient.

Therefore, it should be noted how the dosing reservoir 20 contains a fraction of the reconstituted solution. More precisely, the dosing reservoir 20 isolates said fraction.

Preferably, said third fraction is less than $\frac{1}{25}$ of the reconstituted injectable solution and preferably equal to $\frac{1}{50}$ of the reconstituted injectable solution.

According to one embodiment, the volume of said dosing reservoir 20 is about one milliliter or about one tenth milliliter.

The first plug 6 includes a projecting appendix 16 adapted to pass through the inlet opening 21 of the dosing reservoir 20 and to enter the latter in order to eject the third fraction of solution from the dosing reservoir 20. That happens for and during the administering of the third fraction of solution. Preferably, said projecting appendix 16 has a right cylinder shape more preferably having a circular cross-section.

Preferably, said projecting appendix 16 has a cross-section area equal to or slightly less than that of the inlet opening of the dosing reservoir 20 so that it can enter the dosing reservoir 20 hermetically engaging with the internal walls of the dosing reservoir 20 during its sliding movement inside the latter.

According to one first embodiment the pre-filled injection device 1 includes an opening 23, or a vent channel 23, (from now generally named "vent path") adapted to be passed through by the second solution fraction for the ejection of the second fraction and to allow the projecting appendix 16 to pass through the inlet opening 21 of the dosing reservoir 20.

Figure 6:
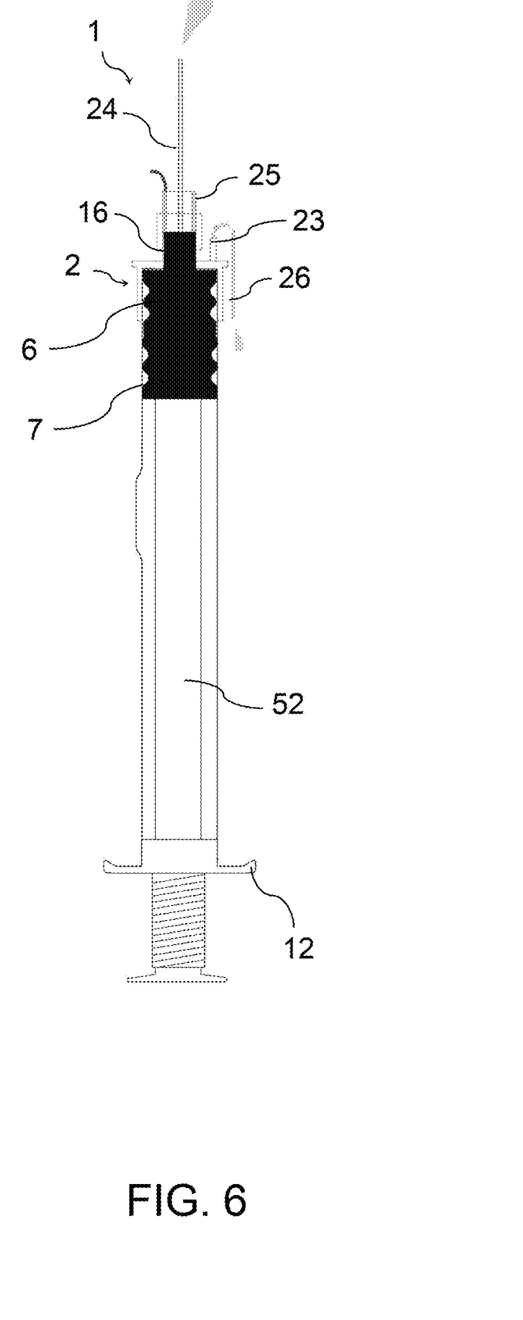
FIG. 6 shows a lateral view of the injection device of FIG. 1 wherein said device is shown in a fifth operating configuration.

As a matter of fact, without said vent path 23 the second fraction of solution, due to liquid incompressibility, would resist the further advance of the first plug 6 that is needed to pass from operating configuration of FIG. 5 to operating configuration of FIG. 6. The latter configuration is named "end of administering configuration". Preferably said vent path 23 is provided for in the closure device 2. Preferably, said vent path 23 is a path initially closed by, for example:

a removable plug; or a removable or openable or pierceable or breakable wall; or a removable or tearable or pierceable membrane; or a valve with manual or automatic opening.

Said vent path 23 is configured to be opened preferably starting from configuration of FIG. 5 in order to allow the pre-filled injection device 1 passing to configuration of FIG. 6.

Said vent path 23 input section faces the inside of the first containment chamber 8, and it is separated from the inlet opening 21 of the dosing reservoir 20 and an output section faces towards the outside of the first containment chamber 8. Preferably, the injection device 1 includes a cannula 26 for ejecting the second solution fraction or an outer collection reservoir of the second solution fraction, and wherein said outlet section is connected or connectable to the cannula 26 or the outer collection reservoir.

From what above described, it should be evident that determining the reconstituted solution quantity to be administered, that is the dose to be injected, in the embodment of FIGS. 1 to 6, is carried out:

ejecting a first fraction of the reconstituted solution from the tubular body 3;

isolating a second fraction of the reconstituted solution in the tubular body 3;

isolating a third fraction of the reconstituted solution inside the dosing reservoir 20;

wherein the second fraction is intended to be ejected through the vent path 23 at the same time the third fraction of reconstituted solution is ejected from the dosing reservoir 20, for administering it.

In one alternative embodiment that will be described in the following referring to FIGS. 7 to 17, instead of the vent path 23 at least one storing reservoir 32, 36 is provided for in the injection device 1, adapted to pass from a closed configuration to an open one following a pressing force being exerted by the first plug 6 against the second fraction of reconstituted solution in order to be filled by the second fraction of reconstituted solution and to allow the projecting appendix 16 passing through the inlet opening of the dosing reservoir 20 and enter into the dosing reservoir 20.

Preferably, the total capacity of the storing reservoir 32, 36 is equal to the capacity of the dosing reservoir 20.

Preferably, the storing reservoir 32, 36 is an annular reservoir.

Figure 7:
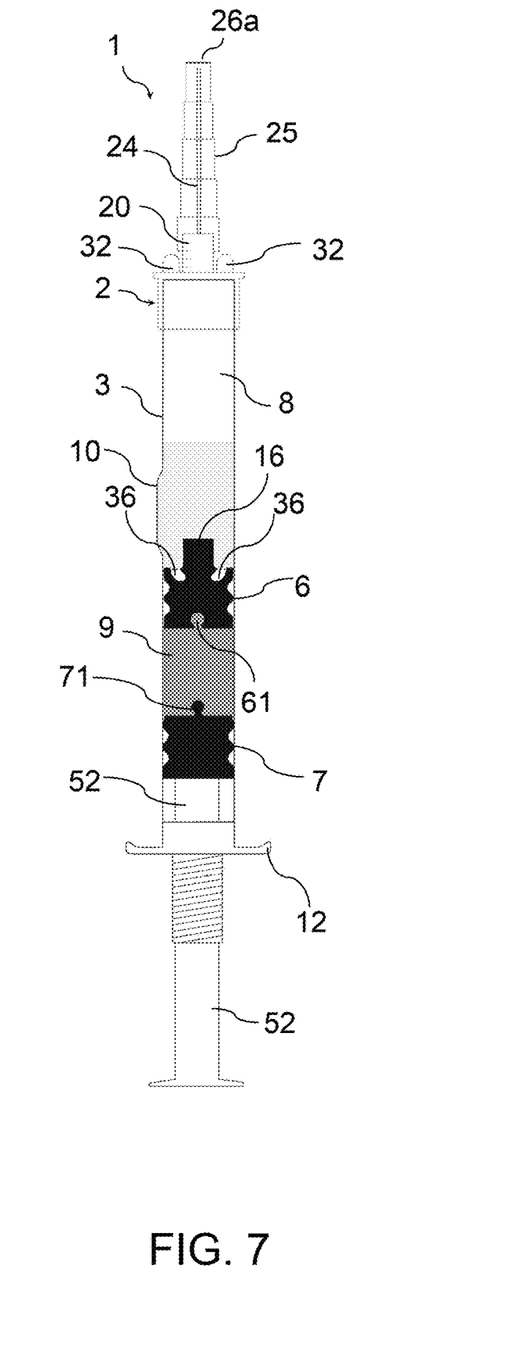
FIG. 7 shows a lateral view of a second embodiment of a pre-filled injection device wherein said device is shown in a first operating configuration.
Figures 8, 9, 10, 11:
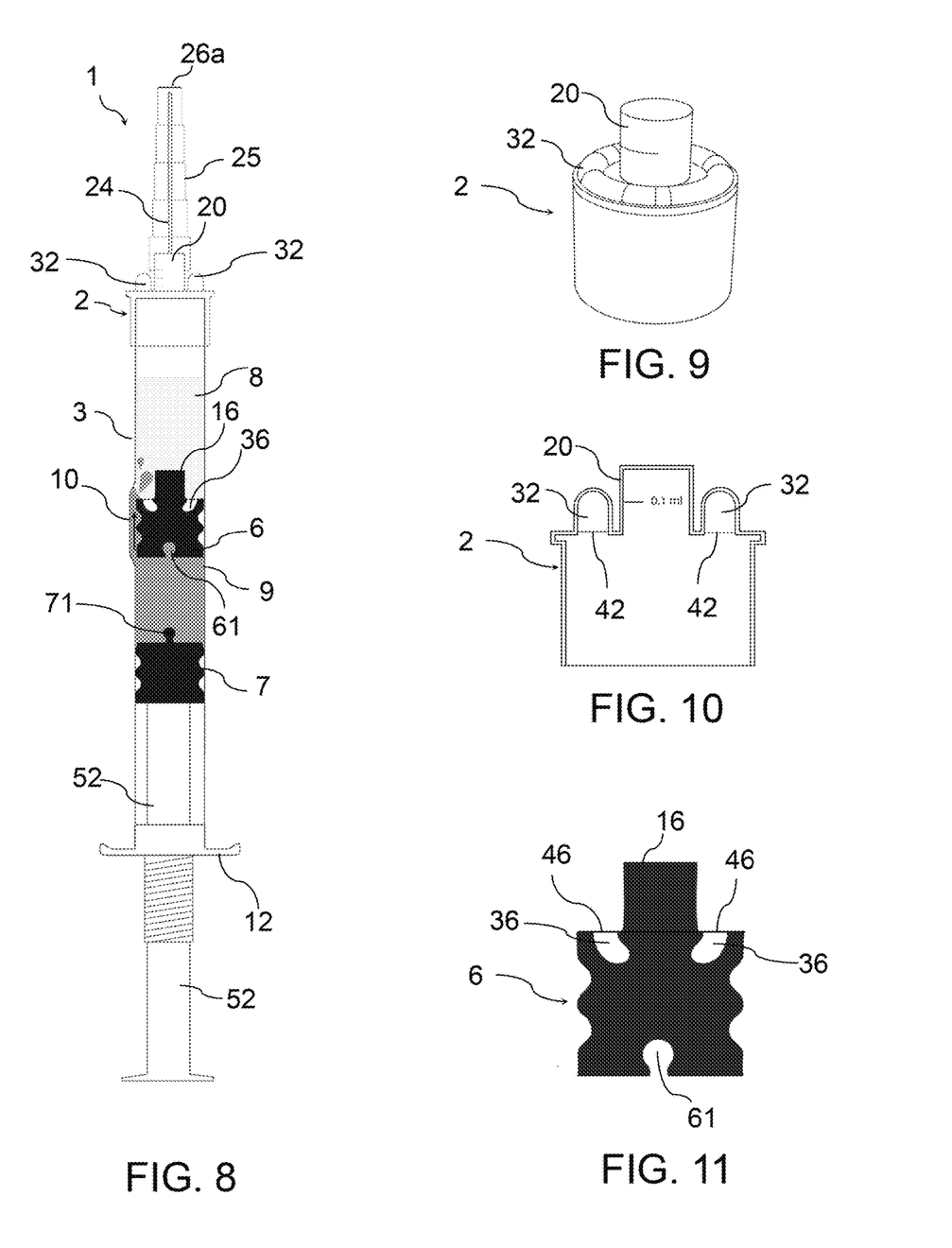
FIG. 8 shows a lateral view of the injection device of FIG. 7 wherein said device is shown in a second operating configuration.
FIG. 9 shows a perspective view of a component of the injection device of FIG. 7.
FIG. 10 shows a cross-section view of the component of FIG. 9.
FIG. 11 shows a cross-section view of a further component of the injection device of FIG. 7.

Referring to FIGS. 9 to 11, according to one embodiment, the storing reservoir 32, 36 is initially occluded by a tearable membrane or film 42, 46, and therefore it cannot initially receive the reconstituted solution. Referring to FIGS. 9 to 11 in the depicted particular example, the storing reservoir comprises two reservoir portions 42 and 46 respectively defined in the closure device 2 and the first plug 6. Each of such storing reservoir portions 42, 46 has an annular and/or semi-toroidal shape, and it is initially closed by a corresponding tearable membrane or film 42, 46. Preferably said two reservoir portions 42, 46 face each other and initially, that is in the operating configuration of FIG. 7, they are on opposite ends of the first containment chamber 8.

Referring to FIG. 7, also in this case initially in the operating configuration being depicted in that figure, named initial configuration, a first 8 and a second 9 containment chamber being hermetically separated from each other are defined inside the tubular body 3. In that configuration, the two reservoir portions 42, 46 are sealed.

Referring to FIG. 8, as already explained for embodiment of FIGS. 1 to 6, starting from the initial configuration of FIG. 7, by applying an external pressing force on plunger 52, the configuration of FIG. 8, also in this case being named reconstitution configuration is reached.

Figure 12:
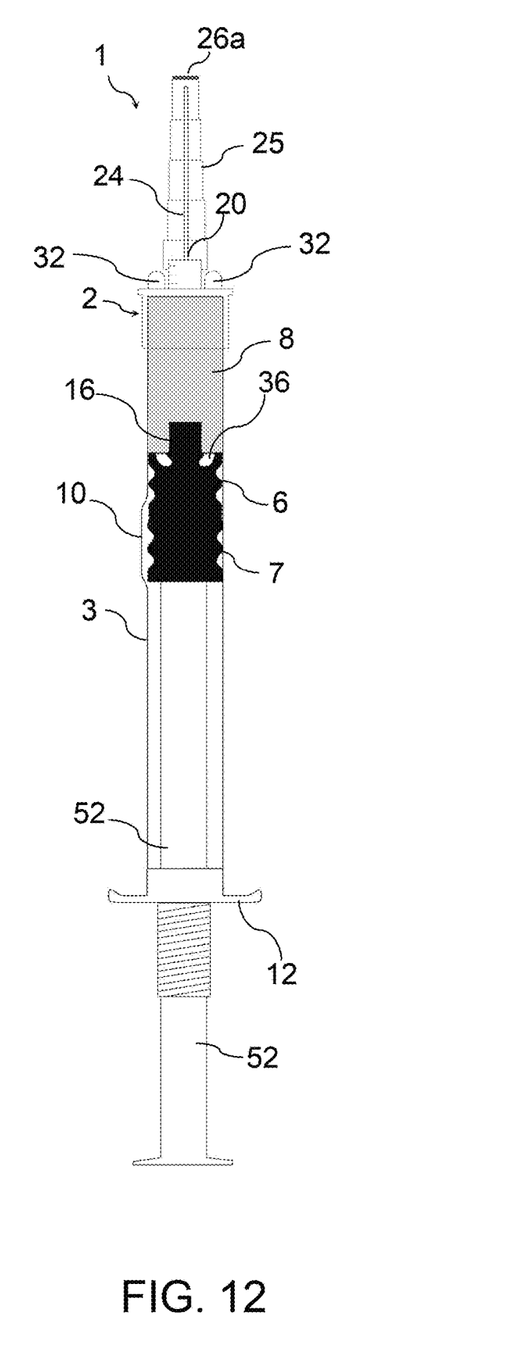
FIG. 12 shows a lateral view of the injection device of FIG. 7 wherein said device is shown in a third operating configuration.

Starting from the reconstitution configuration of FIG. 8 and by going on applying an external pressing force on plunger 52, the configuration of FIG. 12, also in this case being named "end of air ejection" configuration and being equal/similar to the already explained configuration referring to FIG. 4 is reached.

Figure 13:
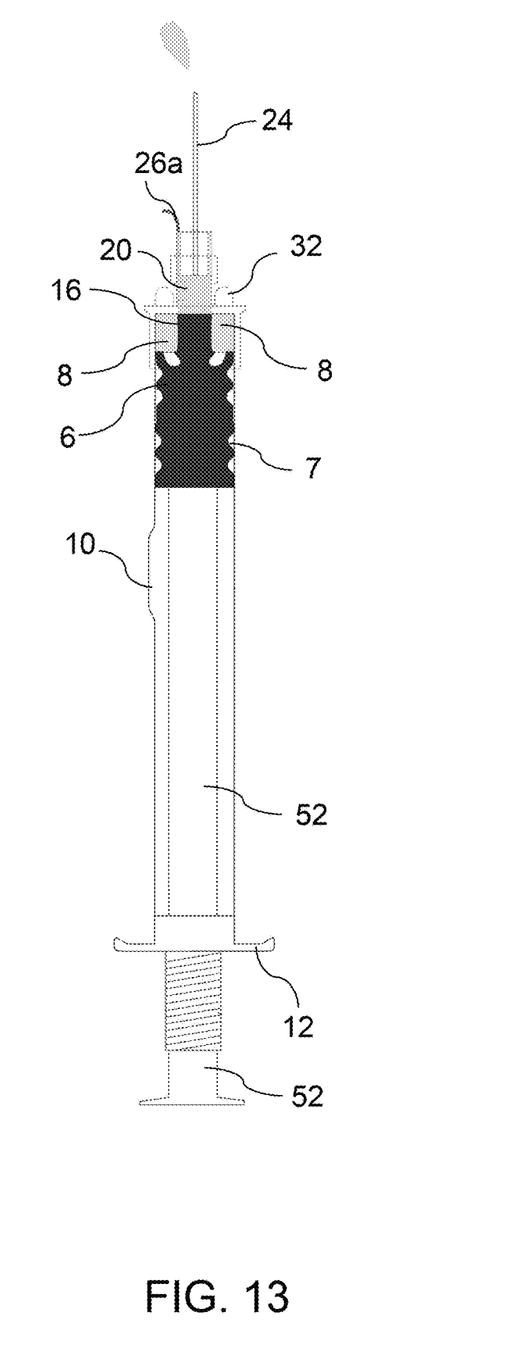
FIG. 13 shows a lateral view of the injection device of FIG. 7 wherein said device is shown in a fourth operating configuration.

Starting from the end of air ejection configuration of FIG. 12 by going on applying an external pressing force on plunger 52, it is possible to slide the first plug 6 (under the pushing action of the second plug 7 being pushed in turn by plunger 52) in order to reduce the volume of the first containment chamber 8 and eject a fraction of the reconstituted solution from tubular body 3 through the outlet opening of the dosing reservoir 20 and therefore through the needle 24, until reaching a so-called pre-administering configuration being depicted in FIG. 13, wherein:

the first plug 6 closes the inlet opening 21 of the dosing reservoir 20;

a second fraction of the injectable solution is contained in the first containment chamber 8; and the dosing reservoir 20 is filled with a third fraction of the injectable solution being a dose to be administered to the patient.

Figure 14:
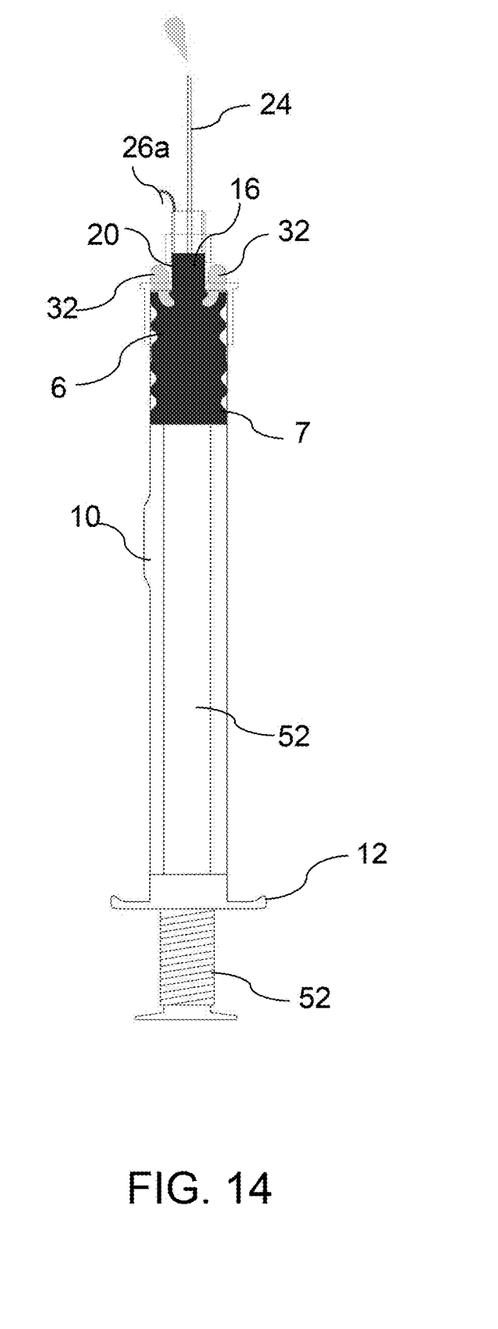
FIG. 14 shows a lateral view of the injection device of FIG. 7 wherein said device is shown in a fifth operating configuration.

Starting from the pre-administering configuration being depicted in FIG. 13, by applying a further pressure on plunger 52, the second fraction of liquid, being incompressible, causes a break or a tear in the tearable films or membranes 42, 46 and causes the second fraction to enter into the storing reservoir 32, 36 as depicted in FIG. 14 (end of administering configuration). In the depicted particular example, the two storing reservoir portions 32, 36 are facing each other in order to define a single toroidal reservoir, which, in the depicted particular example, surrounds the projecting appendix 16 of the first plug 6. At the same time the tearable films or membranes 42, 46 break or tear, the projecting appendix 16 enters into the storing reservoir 20 and the reconstituted solution contained therein is administered through the needle 24.

According to one particularly advantageous embodiment, it is possible to plan that the two plugs 6, are provided with fastening elements, for example engaging elements, which allow the two plugs 6, 7 to be fastened together, once the second plug 7 contacts the first plug 6 and a further pushing force is applied to plunger 52 (in the figures, that happens passing form configuration of FIG. 8 to configuration of FIG. 12). In the depicted particular example, without setting any limitation, said fastening elements include a bulb appendix 71 protruding from the second plug 7 towards the first plug 6 and an opposing conjugated recess 61 being defined inside the first plug 6. As it is possible to realize, the forced entry of the bulb appendix 71 inside the conjugated recess 61 causes the two plugs 6, 7 to couple, making them integral to each other.

Figure 15:
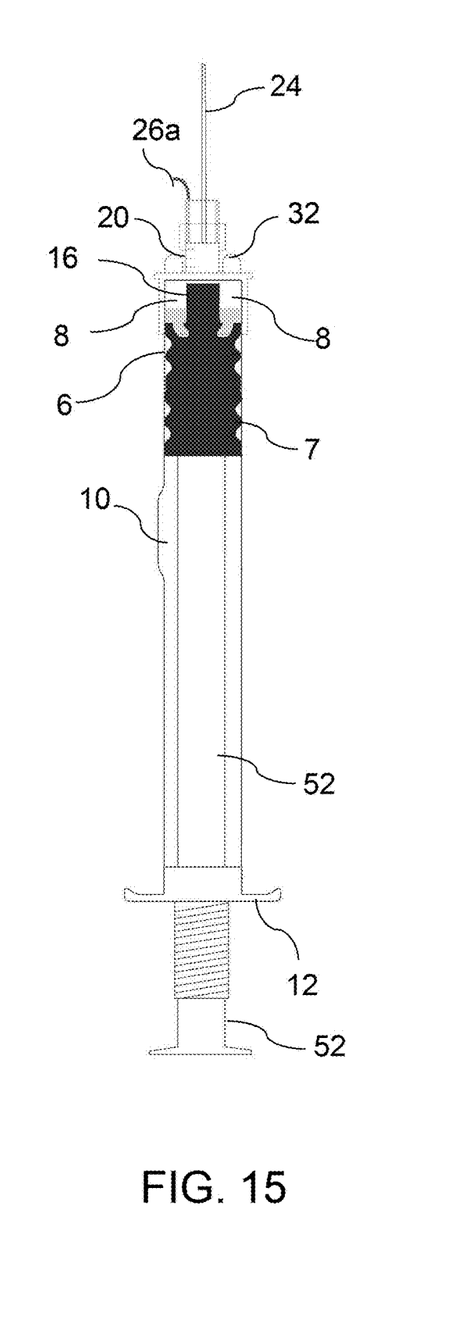
FIG. 15 shows a lateral view of the injection device of FIG. 7 wherein said device is shown in a sixth operating configuration.
Figure 16:
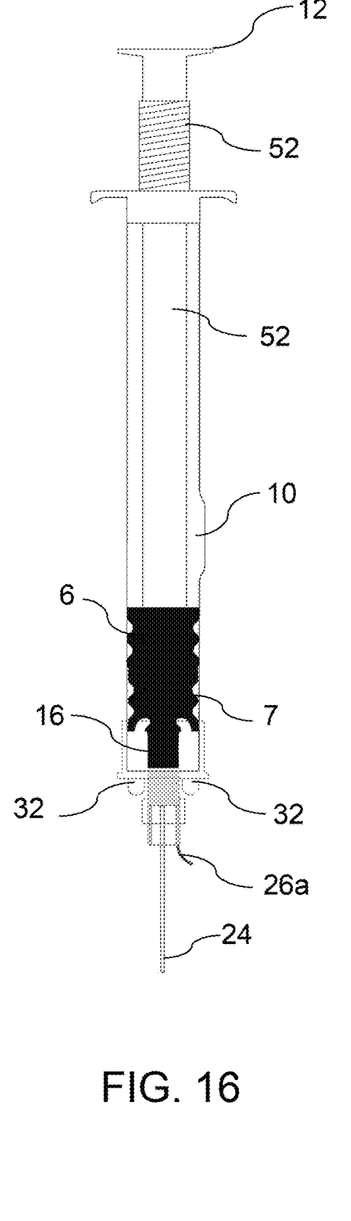
FIG. 16 shows a lateral view of the injection device of FIG. 7 wherein said device is shown in a seventh operating configuration.
Figure 17:
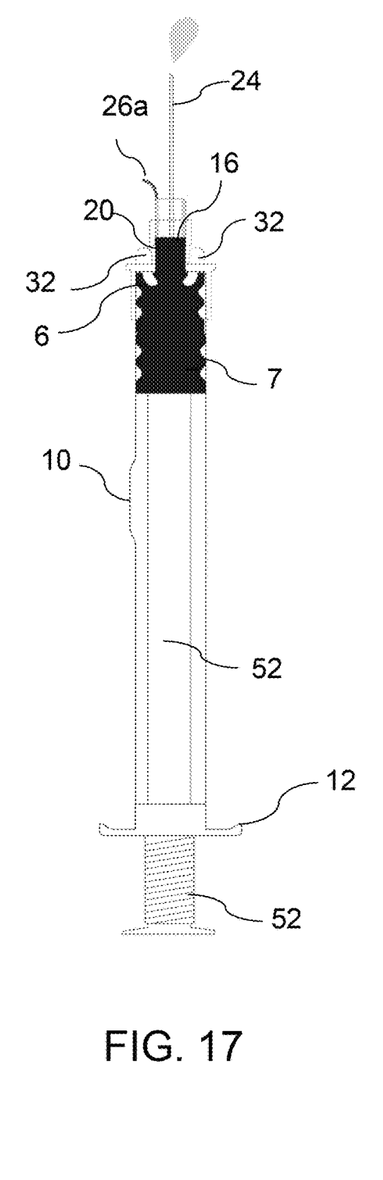
FIG. 17 shows a lateral view of the injection device of FIG. 7 wherein said device is shown in a eightieth operating configuration.

In the above-described different embodiment, which generally concerns the possibility to couple the two plugs 6 and 7 to each other, starting from the configuration of FIG. 14, by exerting an external pulling force on plunger 52, it is possible to move the two plugs 6 and 7 back, until reaching a configuration for example being depicted in FIG. 15 wherein the projecting appendix 16 frees the inlet opening 21 of the storing reservoir 20. By turning the injection device 1 so that the dosing reservoir 20 is oriented downwards, as depicted in FIG. 16, it is possible to drain the second fraction of solution which has been stored in the storing reservoir 36, 36 inside the dosing reservoir 20 and carry out a second administration of the solution, for example in the case the first administration was not successful, then reaching the configuration of FIG. 17, being named end of second administration configuration.

From what described above, it should be evident that determining the reconstituted solution quantity to be administered in the embodiment of FIGS. 1 to 6, is carried out:

ejecting a first fraction of the reconstituted solution from the tubular body 3;

isolating a second fraction of the reconstituted solution in the tubular body 3;

isolating a third fraction of the reconstituted solution inside the dosing reservoir 20;

wherein the second fraction is intended to enter the storing reservoir 32, 36 at the same time the third fraction of reconstituted solution is ejected from the dosing reservoir 20, for administering it.

It should be realized also that in said embodiment, after the first administration, it is possible to reload the dosing reservoir 20 using the second fraction and to carry out a new administration.

The principle of the invention being understood, its embodiments and its embodiment details could be widely changed with respect to what has been described and shown by way of a non-limitative example, without departing form the protection scope as defined in the attached claims.

The invention claimed is:

1. A pre-filled injection device, comprising:
   a tubular containment body extending between a first opening and a second opening, inside which a first containment chamber and a second containment chamber are defined, which are hermetically separated from one another;
   a first solid or liquid substance, contained in the first containment chamber;
   a first plug and a second plug, arranged inside the tubular body so as to define therebetween in the tubular body the second containment chamber, and adapted to slide inside the tubular body;
   a second liquid substance, contained inside the second containment chamber to be mixed inside the tubular body with the first substance for reconstitution of an injectable solution;
   a dosing reservoir separated from the first containment chamber, the dosing reservoir having an inlet opening and an outlet opening, the inlet opening being in communication with the first containment chamber so that the first containment chamber extends between the first plug and the inlet opening of the dosing reservoir;
   the dosing reservoir being adapted to contain a fraction of said injectable solution and isolate said fraction from a second solution fraction of injectable solution contained in the first containment chamber;
   the first plug comprises a projecting appendix adapted to pass through the inlet opening of the dosing reservoir and to enter the dosing reservoir to eject said isolated fraction of solution from the dosing reservoir;
   wherein said device comprises a vent path adapted to be passed through by the second solution fraction for ejection of said second solution fraction and to allow the projecting appendix to pass through the inlet opening of the dosing reservoir and to eject said isolated fraction through said outlet opening.

2. The pre-filled injection device according to claim 1, wherein the vent path has an inlet section which faces into the first containment chamber, and which is separated from the inlet opening of the dosing reservoir, and an outlet section facing an outside of the first containment chamber.

3. The pre-filled injection device according to claim 2, wherein the injection device comprises a cannula for ejecting the second solution fraction or an outer collection reservoir of the second solution fraction, and wherein said outlet section is connected to the cannula or the outer collection reservoir.

4. The pre-filled injection device according to claim 1, comprising at least one storing reservoir adapted to pass from a closed configuration to an open configuration following a pressure force that is exerted by the first plug onto the second solution fraction in order to be filled by the second solution fraction and to allow the projecting appendix to pass through the inlet opening of the dosing reservoir and enter the dosing reservoir.

5. The pre-filled injection device according to claim 4, wherein the overall capacity of the storing reservoir, is equal to the capacity of the dosing reservoir.

6. The pre-filled injection device according to claim 4, wherein the storing reservoir is an annular reservoir.

7. The pre-filled injection device according to claim 1, wherein said projecting appendix is an appendix having a straight cylinder shape.

8. The pre-filled injection device according to claim 1, wherein said projecting appendix has a cross-section that is equal to or less than an area of the inlet opening of the dosing reservoir, so that said projecting appendix may enter the dosing reservoir by sealingly engaging with inner walls of the dosing reservoir during the sliding of the projecting appendix into the dosing reservoir.

9. The pre-filled injection device according to claim 1, wherein only the projecting appendix crosses the inlet opening of the dosing reservoir, and wherein a remaining portion of said first plug and said inlet opening are uncrossed.

10. The pre-filled injection device according to claim 1, wherein said isolated fraction is less than about 1/25 of the reconstituted injectable solution.

11. The pre-filled injection device according to claim 10, wherein said isolated fraction is equal to about 1/50 of the reconstituted injectable solution.

12. A pre-filled injection device, comprising:
a tubular containment body extending between a first opening and a second opening, inside which a first containment chamber and a second containment chamber are defined, which are hermetically separated from one another;
a first solid or liquid substance, contained in the first containment chamber;
a first plug and a second plug, arranged inside the tubular body so as to define therebetween in the tubular body the second containment chamber, and adapted to slide inside the tubular body;
a second liquid substance, contained inside the second containment chamber to be mixed inside the tubular body with the first substance for reconstitution of an injectable solution;
a dosing reservoir separated from the first containment chamber, the dosing reservoir having an inlet opening and an outlet opening, the inlet opening being in communication with the first containment chamber so that the first containment chamber extends between the first plug and the inlet opening of the dosing reservoir;
the dosing reservoir being adapted to contain a fraction of said injectable solution and isolate said fraction from a second solution fraction of injectable solution contained in the first containment chamber;
the first plug comprises a projecting appendix adapted to pass through the inlet opening of the dosing reservoir and to enter the dosing reservoir to eject said isolated fraction of solution from the dosing reservoir;
wherein the projecting appendix has a first maximum width and a remaining portion of the first plug has a second maximum width; wherein the first maximum width is less than the second maximum width.

13. A pre-filled injection device, comprising:
a tubular containment body extending between a first opening and a second opening, inside which a first containment chamber and a second containment chamber are defined, which are hermetically separated from one another;
a first solid or liquid substance, contained in the first containment chamber;
a first plug and a second plug, arranged inside the tubular body so as to define therebetween in the tubular body the second containment chamber, and adapted to slide inside the tubular body;
a second liquid substance, contained inside the second containment chamber to be mixed inside the tubular body with the first substance for reconstitution of an injectable solution;
a dosing reservoir separated from the first containment chamber, the dosing reservoir having an inlet opening and an outlet opening, the inlet opening being in communication with the first containment chamber so that the first containment chamber extends between the first plug and the inlet opening of the dosing reservoir;
the dosing reservoir being adapted to contain a fraction of said injectable solution and isolate said fraction from a second solution fraction of injectable solution contained in the first containment chamber;
the first plug comprises a projecting appendix adapted to pass through the inlet opening of the dosing reservoir and to enter the dosing reservoir to eject said isolated fraction of solution from the dosing reservoir;
at least one storing reservoir adapted to pass from a closed configuration to an open configuration following a pressure force that is exerted by the first plug onto the second solution fraction in order to be filled by the second solution fraction and to allow the projecting appendix to pass through the inlet opening of the dosing reservoir and enter the dosing reservoir;
wherein said storing reservoir is initially occluded by a tearable membrane or film, therefore said storing reservoir cannot initially receive the reconstituted solution.

14. A pre-filled injection device, comprising:
a tubular containment body extending between a first opening and a second opening, inside which a first containment chamber and a second containment chamber are defined, which are hermetically separated from one another;
a first solid or liquid substance, contained in the first containment chamber;
a first plug and a second plug, arranged inside the tubular body so as to define therebetween in the tubular body the second containment chamber, and adapted to slide inside the tubular body;
a second liquid substance, contained inside the second containment chamber to be mixed inside the tubular body with the first substance for reconstitution of an injectable solution;
a dosing reservoir separated from the first containment chamber, the dosing reservoir having an inlet opening and an outlet opening, the inlet opening being in communication with the first containment chamber so that the first containment chamber extends between the first plug and the inlet opening of the dosing reservoir;
the dosing reservoir being adapted to contain a fraction of said injectable solution and isolate said fraction from a second solution fraction of injectable solution contained in the first containment chamber;
the first plug comprises a projecting appendix adapted to pass through the inlet opening of the dosing reservoir and to enter the dosing reservoir to eject said isolated fraction of solution from the dosing reservoir;

at least one storing reservoir adapted to pass from a closed configuration to an open configuration following a pressure force that is exerted by the first plug onto the second solution fraction in order to be filled by the second solution fraction and to allow the projecting appendix to pass through the inlet opening of the dosing reservoir and enter the dosing reservoir;

wherein the storing reservoir comprises a first reservoir portion defined in a closure device and a second reservoir portion defined in the first plug.

15. The pre-filled injection device according to claim 14, wherein each of said reservoir portions has an annular and/or semi-toroidal shape and each of said reservoir portions is initially closed by a corresponding tearable membrane or film.

* * * * *

UNITED STATES PATENT AND TRADEMARK OFFICE
CERTIFICATE OF CORRECTION

PATENT NO. : 10,363,375 B2
APPLICATION NO. : 15/326969
DATED : July 30, 2019
INVENTOR(S) : Ernesto Orofino Page 1 of 1

It is certified that error appears in the above-identified patent and that said Letters Patent is hereby corrected as shown below:

On the Title Page

Item (30) Foreign Application Priority Data: "Jul. 22, 2014 (IT) RM2014A0408" should read -- Jul. 22, 2014 (IT) RM2014A000408 --

Signed and Sealed this
Twelfth Day of November, 2019

Andrei Iancu
*Director of the United States Patent and Trademark Office*